(12) United States Patent
Gorsek

(10) Patent No.: US 6,551,629 B1
(45) Date of Patent: Apr. 22, 2003

(54) CARDIOVASCULAR PROMOTION AND MAINTENANCE COMPOSITION

(75) Inventor: Wayne F. Gorsek, Boynton Beach, FL (US)

(73) Assignee: Vitacost.com, Inc., Boynton Beach, FL (US)

( * ) Notice: Subject to any disclaimer, the term of this patent is extended or adjusted under 35 U.S.C. 154(b) by 0 days.

(21) Appl. No.: 10/187,618

(22) Filed: Jul. 3, 2002

(51) Int. Cl.[7] .................... A61K 35/78; A61K 38/43
(52) U.S. Cl. ................. 424/725; 424/729; 424/766; 424/94.1
(58) Field of Search .................... 424/725, 729, 424/766, 94.1; 514/783; 426/51, 60

(56) References Cited

U.S. PATENT DOCUMENTS 5,846,569 A * 12/1998 Anderson et al. ............ 424/535

\* cited by examiner

Primary Examiner—Christopher R. Tate
Assistant Examiner—Patricia A Patten
(74) Attorney, Agent, or Firm—Hoffman, Wasson & Gitler, P.C.

(57) ABSTRACT

The invention relates to a composition for to assist in the achievement of optimal cardiovascular health. The composition addresses various concerns including low antioxidant status, low levels of essential fatty acids, magnesium, potassium, and elevated levels of homocysteine. It is designated to treat and prevent heart disease and stroke.

4 Claims, No Drawings

CARDIOVASCULAR PROMOTION AND MAINTENANCE COMPOSITION

BACKGROUND OF THE INVENTION

The invention relates to a composition for to assist in the achievement of optimal cardiovascular health. The composition addresses various concerns including low antioxidant status, low levels of essential fatty acids, magnesium, potassium, and elevated levels of homocysteine. It is designated to treat and prevent heart disease and stroke.

The risk factors can be addressed by supplementing a person's diet with a composition containing key vitamins, minerals, antioxidants, and nutrients to promote a healthy cardiovascular system, treat and prevent heart disease and stroke.

Cholesterol is a waxy, oily steroid compound which has received a lot of bad press in recent years—especially when it comes to cardiovascular degeneration. The truth is that cholesterol is vital to the body's health and functioning.

Cholesterol is an essential component in cell membranes. It helps us to absorb fat-soluble vitamins (A, D, E, K) and essential fatty acids. It is also involved in manufacturing key male and female sex hormones and steroidal hormones. These are crucial for a healthy immune system and a smooth running hormonal system. Ironically, a significant percentage of coronary heart disease occurs in people with normal to low cholesterol.

The problem when it comes to heart disease isn't the cholesterol itself—but oxidized cholesterol. That's why supplementing with antioxidants, including natural carotenoid, Vitamins C and E, Coenzyme Q10, as well as herbs, phytonutrients and other nutrients, including amino acids, and alpha lipoid acid all are effective in promoting optimal cardiovascular health.

It is an object of the present invention to provide an unique formulation which allows individuals to maintain the health of the body's cardiovascular system.

SUMMARY OF THE INVENTION

The key to the unique formulation is a combination of effective amounts of specific vitamins, minerals, herbs and nutrients. These essential components in their proper beneficial amounts and forms are proven effective in maintaining cardiovascular health.

The formulation contains Coenzyme Q10, Standardized Green Tea Extract, Standardized Red Wine Extract, Grape Seed Proanthocyanidine, Citrus Bioflavonoids, Chromium, Garlic Extract, Plant Enzymes, Lycopene, Folic Acid, Vitamin B12 and Pyroxidine HCl(Vitamin B6).

The formulation is preferably delivered in capsule form at eight capsules per day.

DETAILED DESCRIPTION OF THE INVENTION

The present invention involves a composition for oral ingestion that contains an effective amount of Coenzyme Q10, Standardized Green Tea Extract, Standardized Red Wine Extract, Grape Seed Proanthocyanidine, Citrus Bioflavonoids, Chromium, Garlic Extract, Plant Enzymes, Lycopene, Folic Acid, Vitamin B12 and Pyroxodine HCl (Vitamin B6) and other minor nutrients. More specifically, this formulated product is a promoter and maintainer of good cardiovascular health. It helps prevent heart attacks, strokes and the onset of arteriosclerosis. This product allows for proper nutrition as a means for substantially promoting cardiovascular health by addressing risk factors such as high homocysteine levels, oxidized cholesterol, and free radical damage.

In order to secure the desired result the following essential components are provided:

Vitamins B6 (100 mg) (10 mg–1,000 mg), B12 (2 mg) (0.2 mg–20 mg) and Folic Acid (800 mcg) (80 mcg–8,000 mcg) have been shown to promote healthy homocysteine levels.

Studies indicate elevated homocysteine may be a 500% greater risk factor for poor cardiovascular health versus elevated cholesterol.

Coenzyme Q10 is a natural nutrient necessary for normal heart function and is vital for cellular energy production. CoQ10 is a powerful antioxidant and free radical scavenger (60 mg)(6 mg–600 mg).

Standardized Green Tea Extract, the most powerful standardized form contains many times the level of active antioxidant compounds compared to non-standardized. Several studies indicate these compounds may protect cholesterol and brain neurons from free radical damage. Green Tea polyphenols may also help block the formation of some potentially toxic compounds, such as nitrosamines, and may stimulate the activity of natural antioxidant and detoxifying enzymes (100 mg) (10-mg–1,000 mg).

Standardized Red Wine Extract (100 mg) (10 mg–1,000 mg), Grape Seed Extract (50 mg)(5 mg–500 mg) and Citrus Bioflavonoids (50 mg) (5 mg–250 mg) have all been shown to significantly delay cholesterol oxidation.

Lycopene (5 mg–100 mg)

In addition to the key components, other components such as Magnesium, Chromium, Garlic Extract, Vitamin A, Vitamin C, Vitamin E, L-Optizinc and other phytonutrients and antioxidant complexes are added.

Betatene—Unlike synthetic beta-carotene, Betatene is natural. It combines a complex of carotenoid found in fruits and vegetables which, as antioxidants, protect cells from free radical damage (500–5000 IU).

Ester C—This patented, pH-balanced/non-acidic form of Vitamin C is required for collagen formation, healthy strong blood vessels and joint health. Bioflavonoids are powerful antioxidants included to enhance Vitamin C (100 mg–10,000 mg).

Natural Vitamin E is 2.6 times more bio-available than synthetic Vitamin E. This nutrient is extremely important for proper immune function and promoting healthy circulation (80–8,000 IU).

L-OptiZinc has been shown to support immune function and has free radical scavenging up to 20 times more than other forms of Zinc. L-OptiZinc was shown to protect the brain and liver. L-OptiZinc may also reduce cellular damage caused by several very dangerous free radicals (1.5 mg–150 mg).

Phytonutrient & Herbal Antioxidant Complex—No other supplement combines Green Tea, Red Wine and Grape Seed Extracts, plus Alpha Lipoic Acid, Coenzyme Q10, Garlic and more.

Although the invention has been described primarily in connection with special and preferred embodiments, it will be understood that it is capable of modification without departing from the scope of the invention. The following claims are intended to cover all variations, uses, or adaptations of the of the invention, following, in general the principles thereof and including such departures from the present disclosure as come within known or customary practice in the field to which the invention pertains, or as are obvious to persons skilled in the field.

The following table depicts a preferred formulation:

|  | Amount per serving | % daily value |
|---|---|---|
| Vitamin A[1] - (Betatene) (as natural carotenoid beta carotene, alpha carotene, lutein, zeaxanthin, cryptoxanthin and palmitate) | 5,000 IU | 100% |
| Vitamin C[2] - (as magnesium ascorbate) | 1 g (1,000 mg) | 1,668% |
| Vitamin D3 (as cholecarciferol) | 400 IU | 100% |
| Natural Vitamin E (as d-alpha tocopherol succinate, gamma, delta and beta) | 800 IU | 2,666% |
| Thiamine (Vitamin B1 HCl) | 200 mg | 13,333% |
| Riboflavin (Vitamin B2) | 10 mg | 588% |
| Niacin (Vitamin B3) | 100 mg | 500% |
| Pyridoxine HCL (Vitamin B6) | 100 mg | 5,000% |
| Folic Acid (as folacin) | 800 mcg | 200% |
| Vitamin B12 (Methylcobalamin) | 2 mg | 33,332% |
| Biotin | 2 mg | 667% |
| Pantothenic Acid (Vitamin B5 as d-calcium pantothenate) | 100 mg | 1,000% |
| Magnesium (from Ester C) | 68 mg | 17% |
| Magnesium (from 1105 mg Citrate) | 232 mg |  |
| Zinc[3] (as L-monomethionine) | 15 mg | 100% |
| Selenium (Selenomethionine) | 200 mcg | 288% |
| Copper (as chelate) (AAC) | 1 mg | 50% |
| Manganese (as chelate) (AAC) | 1 mg | 50% |
| Chromium[4] (as chromium polynicotinate) (Chromemate) | 400 mcg | 333% |
| Molybdenum (as chelate) (AAC) | 150 mcg | 200% |
| Garlic (as aged odorless) (standardized 10,000 ppm allicin) | 900 mg | ** |
| CoEnzyme Q10 | 60 mg | ** |
| Alpha Lipoic Acid | 100 mg | ** |
| Black Pepper[5] (piper nigrum) (fruit extract) (Biopreine) | 5 mg | ** |
| Bioflavonoid (Citrus BioComplex Standardized to 50%) | 50 mg | ** |
| Bioflavonoids (Hesperidin) | 50 mg | ** |
| Bioflavonoids (rutin) | 50 mg | ** |
| Bioflavonoids (quercetin) | 100 mg | ** |
| Grape Seed Extract[6] (Activin ™) | 50 mg | ** |
| Red Wine Extract (Standardized 30% polyphenols) | 100 mg | ** |
| Green Tea Extract (standardized 98% polyphenols, 80% Catechins, 45% EGCG) |  |  |
| Plant Enzymes (Amylase 2,000 SKB, Cellulase 25 CU, Protease 7,500 HUT, Lipase 25 FIP and Lactase 250 ALU) | 200 mg | ** |
| Inositol (as Hexaniacinate) | 200 mg | ** |
| Inositol | 50 mg | ** |
| Ginkgo Biloba (Ginkoaceace) (Leaves) (standardized 24% ginkgo flavon glycosides, 6% terpene lactones) | 120 mg | ** |
| Lutein Extract (from 120 mg FloraGLO) | 6 mg | ** |
| Lycopene[7] (from 100 mg Lyc-o-Mato) | 5 mg | ** |
| Trimethylglycine (betaine HCL) | 200 mg | ** |
| L-Carnitine (Fumerate) | 250 mg |  |
| L-Proline | 100 mg | ** |
| L-Lysine HCL | 100 mg | ** |

* Daily Value Not Established
Other Ingredients: Magnesium Stearate, Silica and Kosher Gelatin (capsule)
Please Note:
1,000 mcg (microgram) = 1 mg (milligram)
1,000 mg = 1 g (gram)

What is claimed is:

1. A cardiovascular maintenance composition comprising an effective amount of:

Pyroxodine HCL;

Folic acid;

Vitamin B12;

Coenzyme Q10;

Citrus Bioflavonoids;

Lycopene; and

Standardized green tea extract, standardized red wine extract and standardized grape seed extract.

2. The cardiovascular maintenance composition of claim 1, wherein the Vitamin B12 is methylcobalamin.

3. The cardiovascular maintenance composition of claim 1, further comprising Vitamin A.

4. A cardiovascular maintenance composition comprising:

100 mg pyroxodine HCL;

800 mcg Folic acid;

2 mg Vitamin B12;

60 mg Coenzyme Q10;

50–250 mg Citrus Bioflavonoids;

5–100 mg Lycopene; and 100 mg Standardized green tea extract, 100 mg standardized red wine extract and 50 mg standardized grape seed extract.

* * * * *